United States Patent [19]

Monroe

[11] Patent Number: 5,213,562
[45] Date of Patent: May 25, 1993

[54] METHOD OF INDUCING MENTAL, EMOTIONAL AND PHYSICAL STATES OF CONSCIOUSNESS, INCLUDING SPECIFIC MENTAL ACTIVITY, IN HUMAN BEINGS

[75] Inventor: Robert A. Monroe, Nelson County, Va.

[73] Assignee: Interstate Industries Inc., Faber, Va.

[21] Appl. No.: 514,460

[22] Filed: Apr. 25, 1990

[51] Int. Cl.$^5$ ............................................. A61M 21/00
[52] U.S. Cl. ....................................... 600/28; 128/732
[58] Field of Search ..................................... 600/26–28; 128/731–732, 905

[56] References Cited

U.S. PATENT DOCUMENTS

| | | |
|---|---|---|
| 2,466,054 | 4/1949 | Siebel . |
| 3,160,159 | 12/1964 | Hoody et al. . |
| 3,576,185 | 4/1971 | Schulz et al. . |
| 3,712,292 | 1/1973 | Zentmeyer, Jr. . |
| 3,753,433 | 8/1973 | Bakerich et al. . |
| 3,826,243 | 7/1974 | Anderson . |
| 3,837,331 | 9/1974 | Ross . |
| 3,884,218 | 5/1975 | Monroe ................................. 600/28 |
| 4,034,741 | 7/1977 | Adams et al. . |
| 4,141,344 | 2/1979 | Barbara . |
| 4,227,516 | 10/1980 | Meland et al. . |
| 4,335,710 | 6/1982 | Williamson . |
| 4,573,449 | 3/1986 | Warnke . |
| 4,834,701 | 5/1989 | Masaki ................................. 600/28 |
| 5,036,858 | 8/1991 | Carter et al. ........................ 128/732 |

*Primary Examiner*—Lee S. Cohen
*Assistant Examiner*—John P. Lacyk
*Attorney, Agent, or Firm*—Sughrue, Mion, Zinn, Macpeak & Seas

[57] ABSTRACT

A method having applicability in replication of desired consciousness states; in the training of an individual to replicate such a state of consciousness without further audio stimulation; and in the transferring of such states from one human being to another through the imposition of one individual's EEG, superimposed on desired stereo signals, on another individual, by inducement of a binaural beat phenomenon.

6 Claims, 5 Drawing Sheets

METHOD OF INDUCING MENTAL, EMOTIONAL AND PHYSICAL STATES OF CONSCIOUSNESS, INCLUDING SPECIFIC MENTAL ACTIVITY, IN HUMAN BEINGS

BACKGROUND OF THE INVENTION

The present invention relates to a method of inducing various states of consciousness in human beings. More particularly, the invention relates to a method of inducing such states of consciousness through generation of stereo audio signals having specific wave shapes which act as a carrier of a binaural beat. The resultant binaural beat acts to entrain brain waves into unique waveforms characteristic of identified states of consciousness. The invention is applicable in areas of learning and behavior replication as well as in the area of sleep inducement, and thus represents a significant departure from and improvement over known audio-based sleep inducement techniques, some of which will be discussed below.

The binaural beat phenomenon was discovered in 1839 by H. W. Dove, a German experimenter. Generally, this phenomenon works as follows. When an individual receives signals of two different frequencies, one signal to each ear, the individual's brain detects a phase difference or differences between these signals. When these signals are naturally occurring, the detected phased difference provides directional information to the higher centers of the brain. However, if these signals are provided through speakers or stereo earphones, the phase difference is detected as an anomaly. The resulting imposition of a consistent phase difference between the incoming signals causes the binaural beat in an amplitude modulated standing wave, within each superior olivary nucleus (sound processing center) of the brain. It is not possible to generate a binaural beat through an electronically mixed signal; rather, the action of both ears is required for detection of this beat.

FIGS. 1A and 1B show two superposed waves of different frequencies. FIG. 1C shows the resulting wave, which has a clear beat phenomenon. Assuming the two waves have equal amplitude but different respective frequencies $f_1$, $f_2$, the combination of the two waves may be represented mathematically as follows:

$$\begin{aligned} X &= x_1 + x_2 \\ &= a^*\cos(2\pi f_1 t) + a^*\cos(2\pi f_2 t) \\ &= a^*[\cos(2\pi f_1 t) + a^*\cos(2\pi f_2 t)] \\ &= 2a^*\cos\left(2\pi \frac{[f_1 - f_2]}{2} t\right) \cdot \cos\left(2\pi \frac{[f_1 + f_2]}{2} t\right) \end{aligned}$$

The beat phenomenon arises from the variation in amplitude of a resulting carrier frequency. Pulses appear every $\frac{1}{2}(f_1-f_2)$, with two maxima occurring each cycle, when $\cos(2\pi)\frac{1}{2}[f_1-f_2]=\pm 1$. That is, the beat frequency is simply $f_1-f_2$, a result which agrees with experience.

Known consciousness state inducing techniques have not used this binaural beat phenomenon, but have relied on other techniques, as follows. For example the use of audio generators to induce a state of consciousness known as sleep is well known in the prior art, as exemplified by U.S. Pat. No. 2,711,165 and 3,384,074. In one type of technique exemplified in these patents, generated audio signals include pleasing and harmonious study sounds or vibrations, fixed frequency signals which are buried cyclically with respect to amplitude, and repetitive sounds such as the falling of rain on the roof and the sighing wind through the trees.

U.S. Pat. No. 2,304,095 relates to a method of inducing sleep by generation of an audible or tactual signal which is related to the physiological process of heartbeat and respiration. In the disclosed method, the pitch and amplitude of a pleasing audio signal are varied at a rate somewhat slower than either the rate of heartbeat or the rate of respiration. As a result, heartbeat and respiration tend to synchronize with the audio signal, thus lowering heartbeat and respiration rates and inducing sleep.

Of course, there are other naturally-occurring sounds which have been recorded, and which are not varied, but which instead induce a state of relaxation which leads to sleep for a similar reason. For example, the pounding of waves on a shore line occurs at a frequency generally lower than that of heartbeat or respiration, and induces a state of relaxation.

The use of an electroencephalogram (EEG) as a research and diagnostic tool has led to findings that particular brain wave patterns are indicative of different states of consciousness. In 1934, researchers discovered that brain waves, and their associated states of consciousness, could be altered with repetitive visual stimulation at a known frequency, an effect known as entrainment. Scientific interest in entrainment continued throughout the 1960's. In the 1970's, numerous independent studies repeatedly confirmed that rhythmic flashing lights rapidly entrained brain waves.

A sonic equivalent of photic entrainment also is known, as disclosed for example in commonly-assigned U.S. Pat. No. 3,884,218, the inventor of which is the inventor of the present application. This patent discloses a method of inducing sleep in a human being by generating an audio signal which is made up of a familiar pleasing repetitive sound modulated by frequencies usually associated with an EEG sleep pattern. There are different EEG patterns related to various levels or depths of sleep, and it has been found that by modulating the repetitive sound with these different sleep patterns, it is possible to induce various levels of sleep. The inventor has coined the term frequency following response, or FFR, to describe this phenomenon.

Other known techniques for inducing various states of consciousness, or for performing brainwave analysis and related functions, are shown, for example, in the following U.S. patents:

| | | | |
|---|---|---|---|
| 2,466,054 | 4,034,741 | 3,160,159 | 4,141,344 |
| 3,576,185 | 4,227,516 | 3,712,292 | 4,335,710 |
| 3,753,433 | 4,573,449 | 3,826,243 | 4,834,701 |
| 3,837,331. | | | |

The binaural beat phenomenon described above also can create a frequency entrainment effect. If a binaural beat is within the range of brain wave frequencies, generally less than 30 cycles per second, the binaural beat will become an entrainment environment. This effect has been used to study states of consciousness, to improve therapeutic intervention techniques, and to enhance educational environments. However, the modulation of the binaural beat signals with brain waves associated with particular activities has not been attempted previously.

SUMMARY OF THE INVENTION

In view of the foregoing, it is one object of the invention to provide a method of inducing states of consciousness by generating stereo audio signals having specific wave shapes. These signals act as a carrier of a binaural beat. The resulting beat acts to entrain brain waves into unique waveforms characteristic of identified states of consciousness.

The method of the invention extends beyond the confines of the frequency entraining concept, and incorporates waveform entrainment by altering the wave shape of the binaural beat. Conventional binaural beat frequency entrainment previously has been limited to conventional wave shapes, i.e., square triangular sinusoidal, or in some cases, the various musical instruments. For example, it is known that radiant energy, such as sound in this case, may be defined by its frequency, amplitude, and wave shape. A musical note is a particularly suitable example of this. Generally, the musical note A above middle C in the twelve tone diatonic scale is assigned a frequency of 440 cycles per second. The amplitude of that note is expressed as the loudness of the signal. However, the wave shape of that note is related strongly to the instrument used. An A played on a trumpet is quite different from an A played on a violin.

The similarity results from the distinct shapes of the waveforms of each instrument. Similarly, human brain waves also have unique wave shapes, wave contours which are neither sinusoidal, nor square, nor triangular, nor like those of any musical instrument.

In accordance with the invention, human brain waves, in the form of EEGs, are superimposed upon specific stereo audio signals, known as carrier frequencies which are within the range of human hearing. Thus the invention relates not only to techniques of generating the binaural beat, but also to specific waveforms of the binaural beat in frequency, waveshape, and amplitude, and most particularly to the source of the data used to produce such waveforms.

DETAILED DESCRIPTION OF THE PREFERRED EMBODIMENT

Figure 1A:
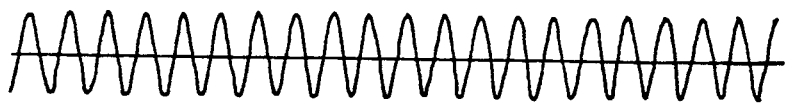
FIGS. 1A-1C show two waves at different frequencies, and the resulting binaural beat, respectively.

As will be discussed below, different regions of the brain produce distinct electrical waveforms during various physical, mental, and emotional states of consciousness. In the method of the invention, binaural beat audio wave shapes are made to match such particular brain waves as they occur during any mental physical, and emotional human condition of consciousness. Thus, it is possible to convert waveforms from specific brain regions, as well as complete brain surface electrical topography.

In the audio application of the invention, using sampled EEG waveforms from a subject in specific states of consciousness and activity, mental and/or physical, these waveforms are impressed upon multiple sets of sound carrier waves within the human spectrum of hearing. Thus, the waveforms translate into wave amplitude modulations of the carrier to effect what is called a frequency following response, or FFR, as mentioned above.

Some description of the empirical procedure used in the course of developing the invention will be useful. as background. In the 1970s, testing was done on various subjects for effective EEG frequencies using audio signals as a human stimulus. Such frequencies were replicated as amplitude modulation of single-channel audio signals within human hearing ranges, for use in sleep-inducing, attention-focusing, etc.

Where particular subjects responded especially well, those signals were converted to binaural beat patterns. The binaural beat signals were derived by first selecting frequencies of the single-channel audio signals based on the well-known "Oersted Curve", named after the famous 19th century physicist. Using this curve permitted selection of specific audio frequencies to provide the greatest binaural beat frequencies at a much lower range. The effectiveness of the tests were doubled as a result of using binaural beat signals.

In the mid 1980s, EEG waveforms themselves were examined as produced by the binaural signals employed. FFR and entrainment factors thought to be responsible for success were verified. One of the results identified as the probable cause of such effectiveness was the synchronization of the brain hemispheres in such signal frequency ranges (i.e. the induced signals were present simultaneously in major portions of both brain hemispheres).

Experimentation expanded to different subjects in similar states of consciousness. Isolation of EEG patterns in these states of consciousness, and conversion of these patterns to binaural sound, with subsequent reapplication of the binaural sounds produced significantly enhanced results. The effect was especially apparent among naive subjects.

Recently, EEG neuromapping began of subjects with particular talents, where those subjects could utilize those talents (e.g. playing a piano sonata, or solving a mathematical equation) at a mental or visualization level. It was possible to isolate the EEG waveforms related to utilization of those talents, and to convert those waveforms to binaural sound. Subsequent exposure of the subject to such patterns enhanced the individual's ability to replicate the process. Exposing other subjects to the signals produced a learned response through repetition.

Thus, the inventor believes that the inventive process, while not necessarily creating a musician or a mathematician, will set up an EEG ambiance in which learning will be facilitated.

Figure 2A:
FIGS. 2A-2D show an input wave, two stereo carrier waves as determined by Fourier analysis, and the resultant binaural beat wave, which matches the contour of the input wave.
Figure 2B:
Figure 2C:
Figure 2D:
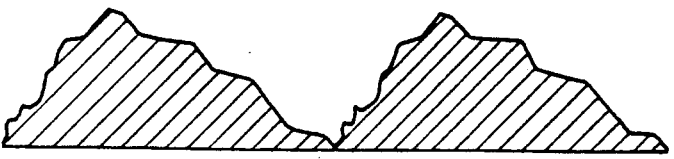

Looking more closely now at the implementation and effects of the invention, FIGS. 2A-2D show a phenomenon wherein an input brain wave signal from a particular brain region is superimposed on stereo carrier waves. FIG. 2D shows the resultant binaural beat wave which matches the contour of the input wave.

The generation and propagation of the binaural beat may be understood from the following series of equations, based on the following.

Figure 1B:
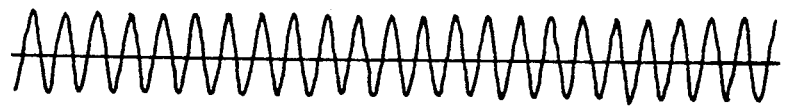
Figure 1C:
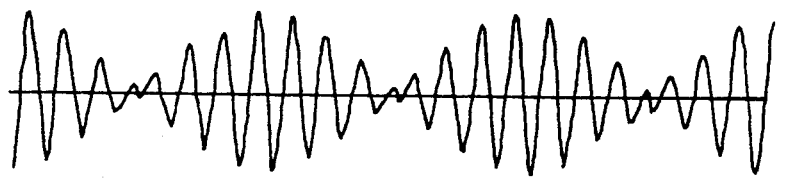

Taking the components from FIGS. 1A-1C, and scaling each component to an appropriate factor (say, α and β).

These components could be recombined to form a beat in accordance with the original components. Linearity and orthogonality principles make these manipulations possible. First, assign the measured wave to be the beat frequency, x.

$$x = \alpha - \beta$$

From the beating waves discussed with respect to FIGS. 1A-1C:

$$\sin(\alpha) + \sin(\beta) = 2\cos\left(\frac{\alpha - \beta}{2}\right)\sin\left(\frac{\alpha + \beta}{2}\right) =$$

$$2\cos\left(\frac{x}{2}\right)\sin\left(\frac{2\alpha - x}{2}\right)$$

$$\cos(\alpha) + \cos(\beta) = 2\cos\left(\frac{\alpha - \beta}{2}\right)\cos\left(\frac{\alpha + \beta}{2}\right) =$$

$$2\cos\left(\frac{x}{2}\right)\cos\left(\frac{2\alpha - x}{2}\right)$$

Now, let us alter the Fourier series f(x) to produce the beat in the shape of the original wave, f'(x):

$$f(x) = \frac{1}{2}a_0 + \frac{1}{2}\sum_{n=1}^{\infty}\cos\left(\frac{nx}{2}\right)\left[a_n\cos\left(n\frac{2\alpha - x}{2}\right) + b_n\sin\left(n\frac{2\alpha - x}{2}\right)\right]$$

$$= \frac{1}{2}a_0 + \frac{1}{2}\sum_{n=1}^{\infty}\cos\left(n\frac{\alpha - \beta}{2}\right)\left[a_n\cos\left(n\frac{\alpha + \beta}{2}\right) + b_n\sin\left(n\frac{\alpha + \beta}{2}\right)\right]$$

$$= \frac{1}{2}a_0 + \frac{1}{2}\sum_{n=1}^{\infty}\cos\left(n\frac{\alpha - \beta}{2}\right)a_n\cos\left(n\frac{\alpha + \beta}{2}\right) + \cos\left(n\frac{\alpha - \beta}{2}\right)b_n\sin\left(n\frac{\alpha + \beta}{2}\right)\right]$$

$$= \frac{1}{2}a_0 + \frac{1}{2}\sum_{n=1}^{\infty} a_n[\cos(\alpha) + \cos(\beta)] + b_n[\sin(\alpha) + \sin(\beta)])$$

$$= \frac{1}{4}a_0 + \frac{1}{2}\sum_{n=1}^{\infty}[a_n\cos(\alpha) + b_n\sin(\alpha)] + \frac{1}{4}a_0 + \frac{1}{2}\sum_{n=1}^{\infty}[a_n\cos(\beta) + b_n\sin(\beta)]$$

$$= \frac{1}{2}\left\{\frac{1}{2}a_0 + \sum_{n=1}^{\infty}[a_n\cos(\alpha) + b_n\sin(\alpha)]\right\} + \frac{1}{2}\left\{\frac{1}{2}a_0 + \sum_{n=1}^{\infty}[a_n\cos(\beta) + b_n\sin(\beta)]\right\}$$

$$= \frac{1}{2}g(\alpha) + \frac{1}{2}h(\beta)$$

From the foregoing, it can be seen readily that $g(\alpha)$ and $h(\beta)$ have become two waves, each having half the amplitude of the original wave, the combination of these waves producing a beat which is the input shape f(x).

Thus, using two-channel stereo sound, it is possible to modulate two separate sets of carrier waves so that the replicated EEG waveforms are created as differential beat frequencies between the separate sets. Thus, the method permits the direct application on a frequency base without having to consider the limitation of the spectrum of human hearing. The brain itself synthesizes the signals which cause the effect.

One example may be as follows. If a carrier frequency of 100 Hz were employed in one channel of the audio signal, and a carrier frequency of 104 Hz were employed in the other channel, a binaural beat of 4 Hz would result. In EEG waveform synthesis, as many as 100 separate carrier pairs may be used or a single broadbanded carrier pair may be used to generate a similar number of specific binaural beats that replicate the EEG waveforms in both frequency and amplitude.

A 4 Hz, or a 5 Hz binaural beat would be too low in frequency to hear. Using the Oersted curve mentioned above, the most effective harmonic carrier would be 275 Hz, which is within hearing range. For the multiple waveform situation just discussed, the differential between carrier waves on a single channel also is utilized to produce an FFR.

One type of audio pattern found to be particularly useful in implementing the inventive method is what is known to the inventor as Phased Pink Sound. The full spectrum of audible sound is known commonly as "white" noise. "Pink" sound is known to result from an adjustment in amplitude of white sound to compensate for decline in perception by the human ear at both ends of the audible spectrum.

Phased Pink Sound results from the relative rotational shifting of pink sound from one stereo audio channel to another with cyclic changes in amplitude, frequency, and rate of panning. Such changes generally are synchronous with selected waveforms within the multiple patterns of the binaural beat generating system. Studies have shown that using Phased Pink Sound at a level at least 10 dB lower than the binaural beat signals produces as much as a 30% enhancement in FFR within the EEG waveforms of the listening individual. There is some basis for concluding that Phased Pink Sound provides an audio base that assists the brain in "synthesizing" the binaural beat frequencies normally inaudible in the human hearing process.

Basically, Phased Pink Sound is generated by a digital processor, which converts mathematical sequences, derived from appropriate algorithms, into audible sound. Such digital processors and their operation are well-known in the art, and so are not discussed here. Inherent in such a system is a frequency sensor that synchronizes the phasing with dominant EEG waveforms as those waveforms are introduced from another source.

Examples of suitable algorithms for implementing Phased Pink Sound are as follows:

```
/************************************************************
 * Algorithm to generate 8-bit PCM samples in array pink[] of the  *
 * single channel sound that serves as the source for the stereo  *
 * "phased pink" sound                                            *
 ************************************************************/ include <math.h>
include <stdio.h> define M2PI   -6.283185307179586
define SAMPLES_PER_SECOND 10466.5
#define CUTOFF 200.0        /* cutoff frequency for low-pass filter */
#define S 83732             /* number of samples to generate */
#define MINDELAY 60         /* minimum flanging delay (samples) */
define MAXDELAY 80         /* maximum flanging delay (samples) */ extern short w[];           /* 8192 entry table of 16-bit sine values
                               scaled from 0x8001 to 0x7FFF */
extern double st_entries;   /* count of entries in sine table */ long phase;                 /* random number generator phase */
long fa;                    /* filter accumulator */
long fc;                    /* filter constant */
long sweep;                 /* flanging filter phase */
long sweep0;                /* flanging filter initial phase */
long ds;                    /* flanging filter phase step */
long count;                 /* samples remaining in flanging filter cycle */
long count0;                /* samples in flanging filter cycle */
long delay;                 /* current flanging filter delay (XXXX.XXXX) */
long delay0;                /* flanging filter delay constant */
long range;                 /* flanging filter delay range */
short gainNS;               /* noise sound gain (gain = gainNS/1024) */
short gainFS;               /* flanging sound gain (gain = gainFS/1024) */
short noise[S+MAXDELAY];    /* array to receive noise samples */
short offset;               /* final sample offset to balance values */
short scaleF;               /* final scale factor to range samples */
char pink[S];               /* array to receive "phased pink" samples */

/************************************************************
 * Main program                                                   *
 ************************************************************/ main()
{
    long control_base;      /* initial flanging delay */
    long control_range;     /* range of flanging control */
    int i;                  /* loop index */
    short *np;              /* pointer to filtered noise sample array */
    short *fsnp;            /* pointer to initial/final noise sequence */
    short NoiseGen();       /* next filtered noise sample */
    short Flange();         /* flanging sample */
    short xx;               /* output before final scaling */
    /* Initialize the white noise generator */
    phase = 0x8000;
```

```
/* Initialize low-pass filter */
fa = 0;
fc = (1.0 - exp(M2PI * CUTOFF / SAMPLES_PER_SECOND)) * 65536.0;

/* Initialize flanging filter for 8 second cycle.  Delay sweeps
   sinusodially around 5*PI/2.  Flanginging tone gain is 75%
   of the noise tone */
sweep = sweep0 = ((long)((.75 * st_entries) * 65536.0 + 0.5))
   & 0x1FFFFFFF;
control_base = w[sweep0 >> 16];
control_range = 0x0007FFFL - control_base;
range = (((double)(MAXDELAY - MINDELAY) * 32767.0) / control_range)
   * 16.0 + 0.5;
delay0 = (MINDELAY << 16) - control_base * (range >> 3);
ds = (st_entries / (8.0 * SAMPLES_PER_SECOND)) * 65536.0 + 0.5;
count = 8.0 * SAMPLES_PER_SECOND + 0.5;
gainNS = 585;
gainFS = 439;

/* Initialize the final offset and scale factor for these filter
   parameters (empirically determined) */
offset = 153;
scaleF = 0x245;

/* Generate an initial sequence of noise samples to provide for
   delayed samples */
np = fsnp = noise;
for (i = 0; i < MAXDELAY; i++) *np++ = NoiseGen();

/* Generate the next S samples of "phased pink" sound */
for (i = 0; i < S; i++) {

/* Generate the next colored noise sample.  For looping,
      finish off with the initial noise sequence */
   if (i < S-MAXDELAY) *np = NoiseGen();
   else *np = *fsnp++;

/* Apply a sweeping cosine comb filter to flange the sound */
   xx = (*np*gainNS + Flange(np)*gainFS) >> 10;
   pink[i] = ((xx + offset) * scaleF) >> 16;
   np++;

}
}

/***************************************************************
 * NoiseGen -- function to generate a filtered noise sample     *
 ***************************************************************/ short NoiseGen(nsp)
{
   long x;             /* current noise sample */
   long y;             /* current filtered noise sample */

/* Generate sinusodial density noise from white */
   phase = phase << 1;
```

```
if (phase & 0x10000) phase = phase ^ 0x1087;
phase = phase & 0xFFFF;
x = w[phase >> 3];

/* Apply 1st order low-pass digital filter */
y = (fc*fa) >> 16;
fa += (x >> 4) - y;
return((short)(y << 4));
}

/***************************************************************
 * Flange -- function to generate a flanging noise sample       *
 ***************************************************************/ short Flange(nsp)
    short *nsp;         /* pointer to current noise sample */
{
    short f;            /* flanging noise sample */
    short *dnp;         /* pointer to delayed noise sample */

/* Apply a sinusodially sweeping comb filter to flange the sound */
    if (count--) sweep = (sweep + ds) & 0x1FFFFFFF;
    else {
        sweep = sweep0;
        count = count0;
    }

/* Compute the filter delay and linearly interpolate between
       noise samples to simulate a continuously variable delay */
    delay = delay0 + ((w[sweep >> 16] * range) >> 3);
    dnp = nsp - (delay >> 16);
    f = *dnp +
        ((((*(dnp-1) - *dnp) >> 1) * ((delay & 0xFFFF) >> 1)) >> 14);
    return(f);
}
```

Figure 3A:
FIGS. 3A-3B, 3C-3D, 3E-3F, and 3G-3H are pairs of graphs showing a normal waking EEG and FFR responses in different signal ranges, respectively.
Figure 3B:
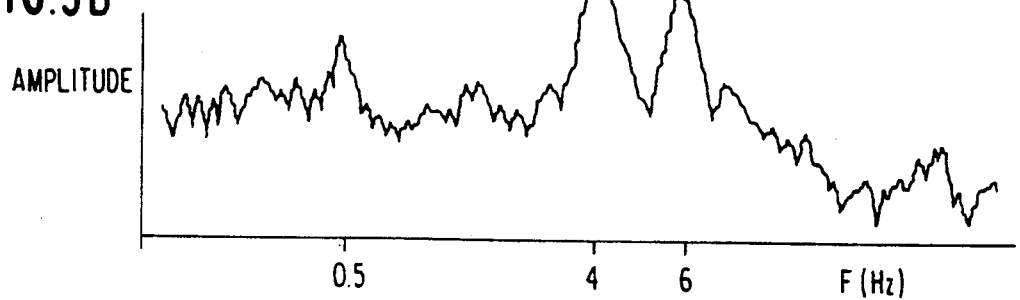

Looking at some results of the inventive method, FIG. 3A shows the EEG of a subject in a normal waking state. FIG. 3B shows an EEG of the individual after listening to binaural beat sounds produced in accordance with the invention. The Figure shows an FFR response in the 1.5, 4, and 6 Hz signal range.

Figure 3C:
Figure 3D:
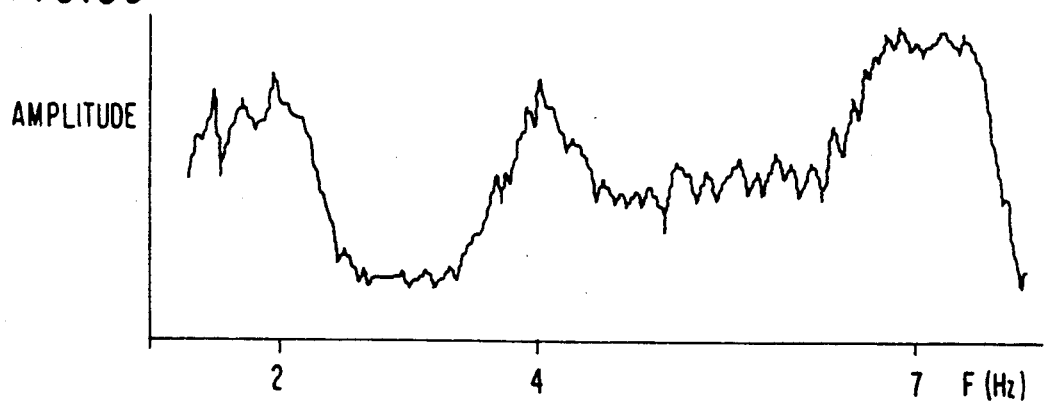

Likewise, FIG. 3C shows the EEG of a subject in a normal waking state, and FIG. 3D shows an EEG of the individual after listening to other binaural beat sounds produced in accordance with the invention. The Figure shows an FFR response in the 2, 4, and 7 Hz signal range.

Figure 3E:
Figure 3F:
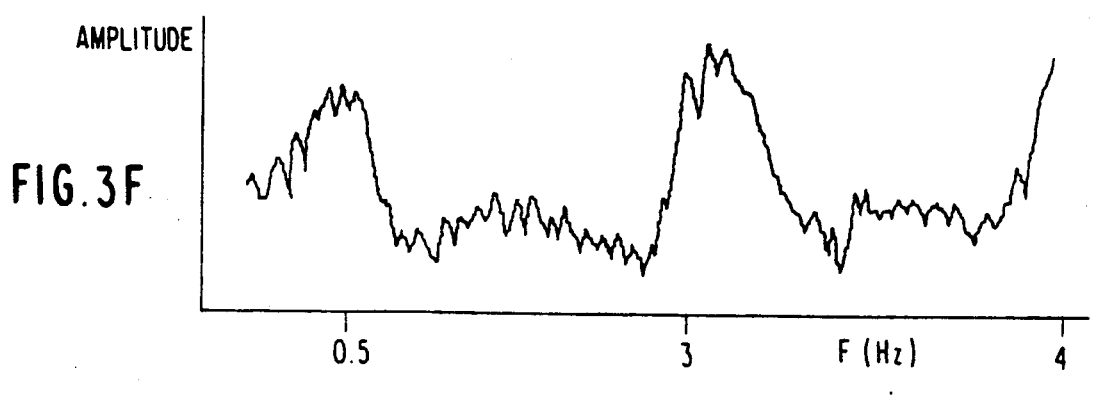

FIG. 3E shows the EEG of a subject in a normal waking state, and FIG. 3F shows an EEG of the individual after listening to still other binaural beat sounds produced in accordance with the invention. The Figure shows an FFR response in the 0.5, 3, and 4 Hz signal range.

Figure 3G:
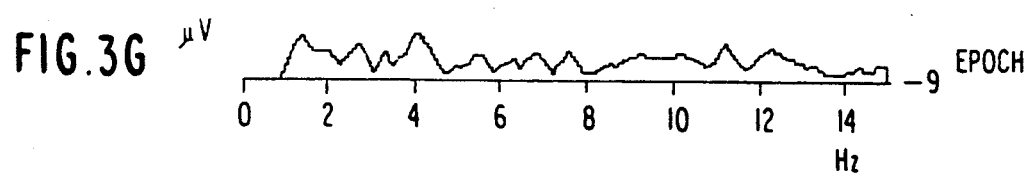
Figure 3H:
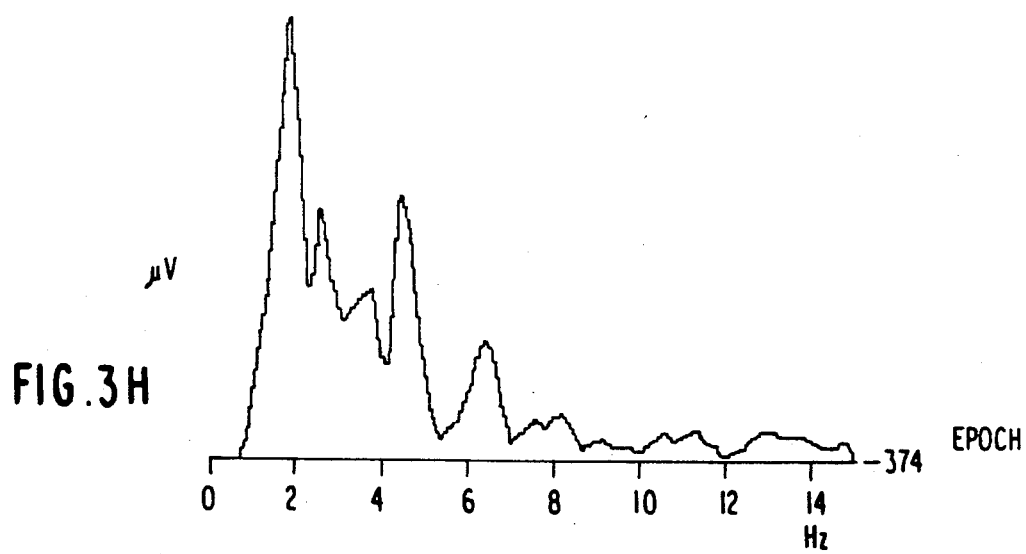

Finally, FIG. 3G shows the EEG of a subject in a normal waking state, and FIG. 3h shows an EEG of the individual after listening to still other binaural beat sounds produced in accordance with the invention. The Figure shows FFR response to 1.5, 2, and 4 Hz signals in amplitude, by frequency.

Figure 4A:
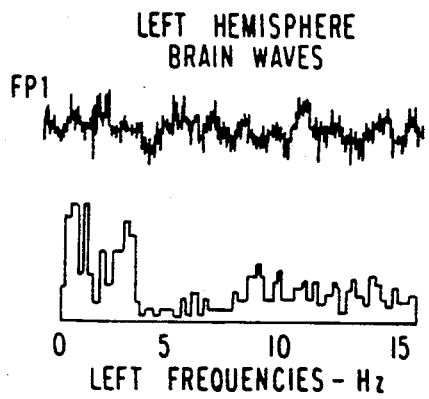
FIGS. 4A-4F show topographic brain maps of the neocortex of a subject in a normal waking state, and after listening to a binaural beat sound pattern.
Figure 4B:
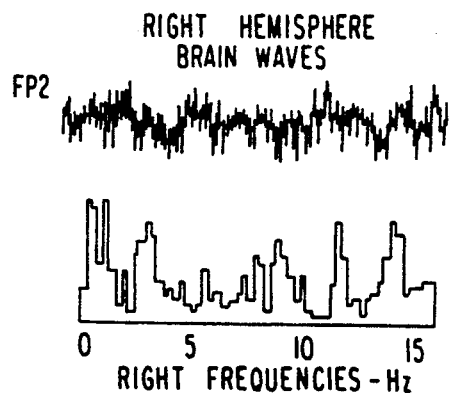
Figure 4C:
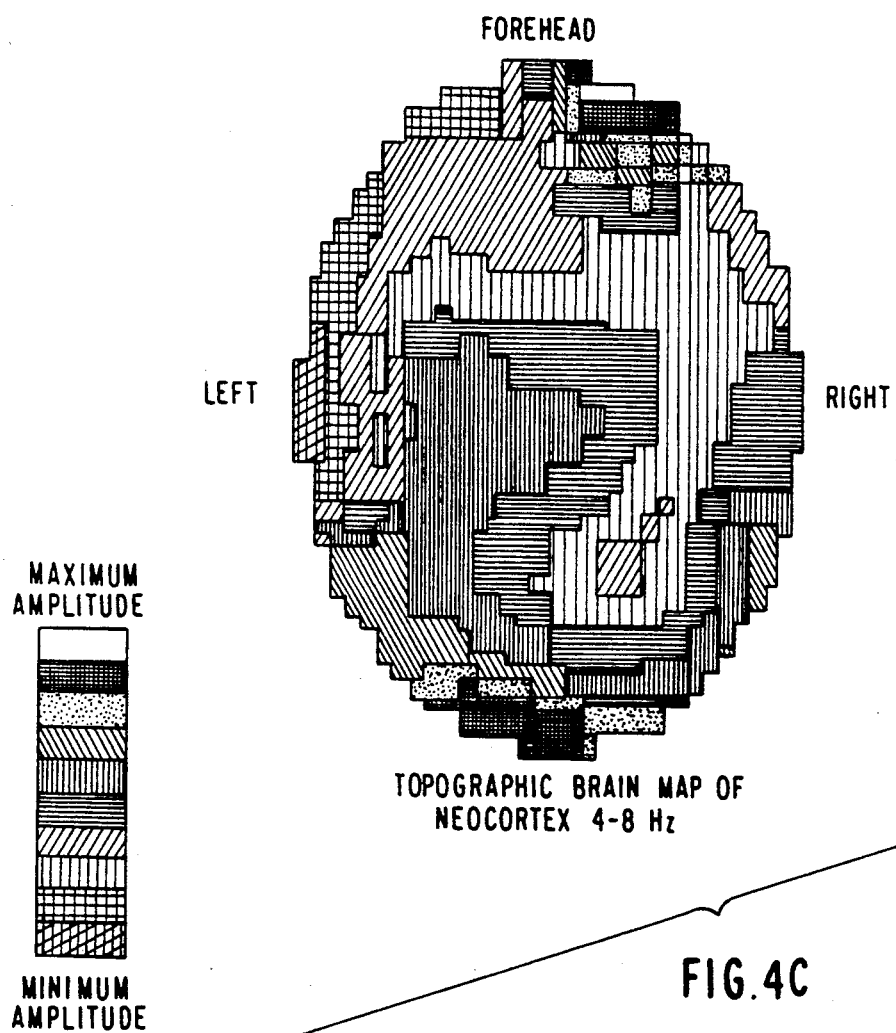

FIGS. 4A-4C shows a typical contour map of a subject in a normal waking state. It should be noted that the map shows a lack of continuity. Note also the lack of significant amplitude patterns ranging between temporal lobes, and the relative lack of intensity within the frontal area.

Figure 4D:
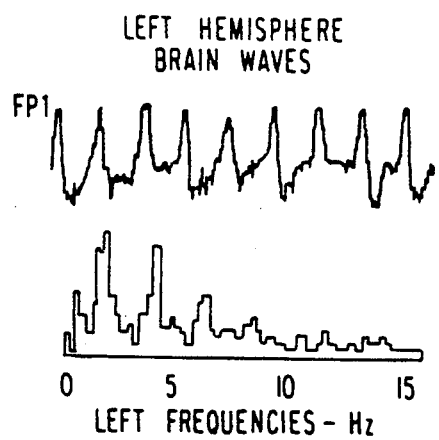
Figure 4E:
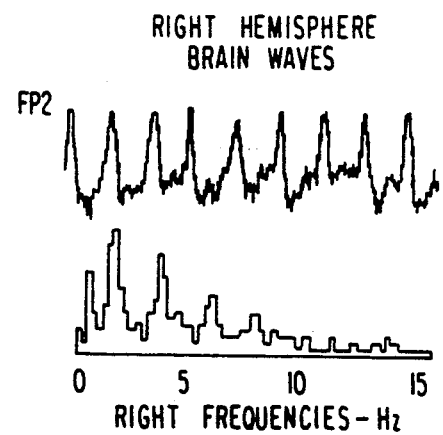
Figure 4F:
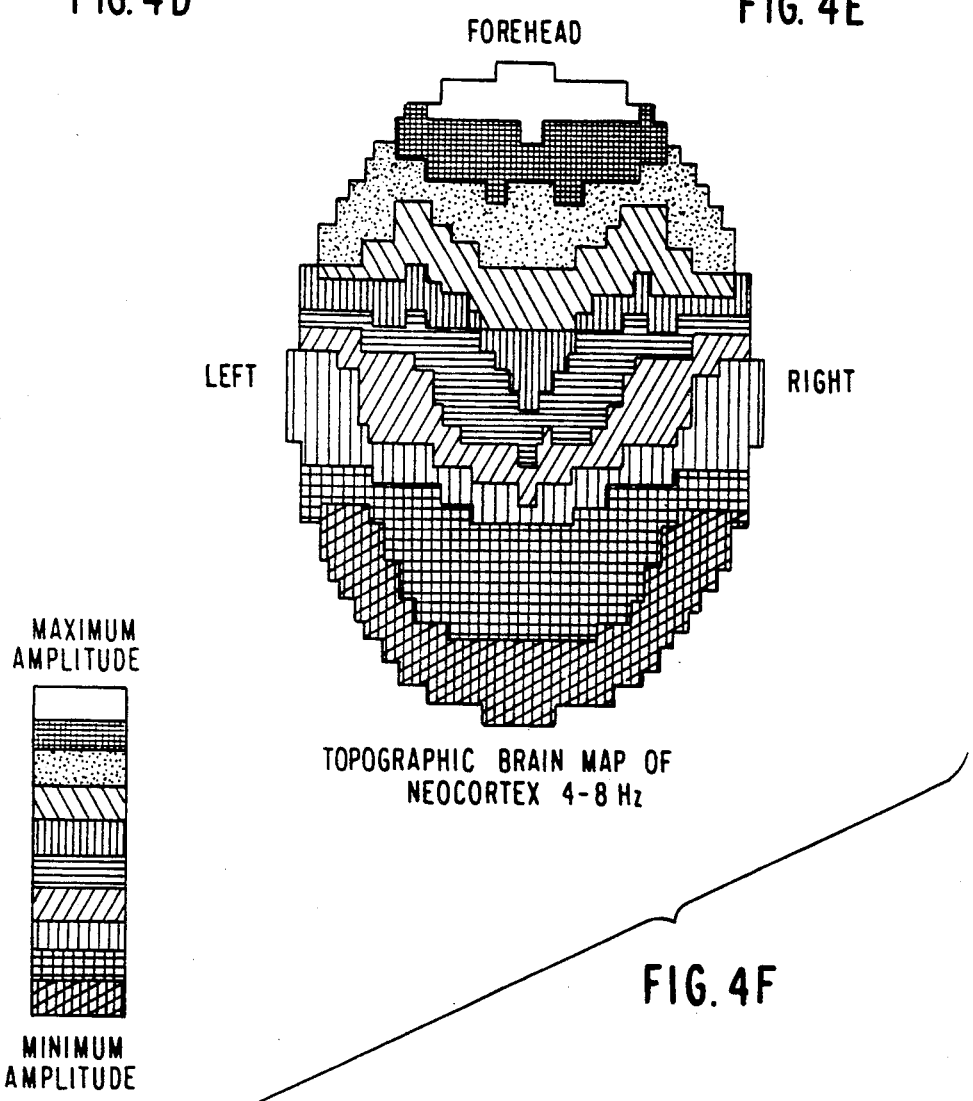

In contrast, FIGS. 4D-4F shows a contour map of the same individual after listening to binaural beat sound in accordance with the invention. Note the synchronization between hemispheres, and the high amplitude of activity at the frontal portion of the brain. Note also how the left and right hemisphere brain waves exhibit significantly higher amplitudes in the frequencies found in the original sound stimulus.

The application of the binaural beat signals by headphones or other second producing devices causes the following results:

1. When such audio signals are provided simultaneously with the state of being itself, those specific states can be enhanced. The additional pattern superposed upon the original provides a powerful setting to maintain and/or expand the condition.
2. By recording the audio signals and playing them back, an individual may return to an original or previously-experienced state of consciousness whenever desired.

3. By listing to recordings of these audio signals, an original pattern or condition induced in one individual may be replicated in other individuals.

4. An individual can be trained, based on sufficient repetition of application of these waveforms, to the point that the individual can recall and replicate these waveforms themselves, without further outside stimulation.

The method of the invention has applications in a number of different areas, not the least of which is the inducement of a state of sleep. Other areas of application include inducement of wakefulness of varying degrees; focusing of attention; inducement of mental and physical relaxation; enhancing intellectual performance in various mental disciplines such as mathematics; enhancement of creativity; the reexperience of previous activity; the acquisition of new abilities which others already have; reinforcement and restoration of weak areas in the mind and body; enhancement and strengthening of mental and/or muscular coordination; and development of integration of entire brain function. Human beings have EEG patterns which are unique to the various states of consciousness and mental and/or physical activity just mentioned, so that the imposition of the appropriate stereo audio signals on the desired EEG wave produces the binaural beat which is necessary to induce the state.

While the invention has been described above in detail with reference to a particular specific embodiment, various modifications within the spirit and scope of the invention will be apparent to those of working skill in this technological field. Thus, the invention should be considered as limited only by the scope of the appended claims.

What is claimed is:

1. A method of inducing states of consciousness in human beings, comprising:
   providing a replicated electroencephalogram (EEG) waveform indicative of a desired state of consciousness;
   superimposing said EEG waveform on two separate sets of carrier waves using stereo sound;
   creating differential beat frequencies between said sets of carrier waves in accordance with said superimposing step; and
   providing the resulting signals in audio form to respective ears of a human being, to induce said state of consciousness.

2. A method as claimed in claim 1, wherein said creating step includes the step of combining pink with said sets of carrier waves by shifting of said pink sound with respect to said EEG waveform from one stereo audio channel to another, with cyclic changes in amplitude, frequency, and rate of panning.

3. A method as claimed in claim 1, wherein all of said steps are performed repeatedly on a particular individual over a period of time so that the individual is able eventually to reproduce said desired state of consciousness without further audio stimulation.

4. A method as claimed in claim 1, wherein all of said steps are performed using the EEG of one individual, but said applying step is carried out with another individual, so as to transfer the desired state of consciousness of one individual to another.

5. A method as claimed in claim 1, wherein said first providing step comprises the step of providing a plurality of EEG waveforms, indicative of different respective states of consciousness, and each of said superimposing, creating, and second providing steps are performed with each of said plurality of EEG waveforms.

6. A method as claimed in claim 1, wherein said second providing step results in substantial synchronization of major portions of both brain hemispheres of said human being.

* * * * *